United States Patent [19]

Takata

[11] Patent Number: 4,941,467
[45] Date of Patent: Jul. 17, 1990

[54] HUMIDIFICATION FACE MASK

[76] Inventor: Danzaburo Takata, 21-B803, Kashikiriyama, Suita-shi, Osaka, Japan

[21] Appl. No.: 324,111

[22] Filed: Mar. 16, 1989

[30] Foreign Application Priority Data

Apr. 19, 1988 [JP] Japan .................................. 63-96343

[51] Int. Cl.⁵ ...................... A61M 15/00; A62B 7/00; A62B 18/02
[52] U.S. Cl. .......................... 128/203.12; 128/203.29; 128/203.11; 128/204.13; 128/206.22
[58] Field of Search ....................... 128/200.11, 200.12, 128/200.13, 203.29, 204.11, 204.13, 206.22, 203.12, 206.27, 206.28

[56] References Cited

U.S. PATENT DOCUMENTS

| 302,949 | 8/1884 | Skene | 128/206.22 |
| 612,295 | 10/1898 | Woodling | 123/204.13 |
| 718,470 | 1/1903 | Jones | 128/203.29 |
| 2,435,721 | 2/1948 | Lehmann | 128/206.22 |
| 3,042,034 | 7/1962 | Gruenewaelder | 128/206.12 |
| 3,814,094 | 6/1974 | De Angelis et al. | 128/201.13 |

FOREIGN PATENT DOCUMENTS

| 73320 | 4/1917 | Austria | 128/204.13 |
| 546686 | 11/1922 | France | 128/204.13 |
| 2411 | of 1875 | United Kingdom | 128/204.12 |
| 24150 | of 1913 | United Kingdom | 128/203.13 |
| 1183262 | 3/1970 | United Kingdom | 128/204.13 |

Primary Examiner—Edgar S. Burr
Assistant Examiner—Kimberly L. Asher
Attorney, Agent, or Firm—Armstrong, Nikaido, Marmelstein, Kubovcik & Murray

[57] ABSTRACT

A humidification face mask comprises an inner mask member and an outer mask member which are bonded together in a sealed manner along the lower and side edges to define therebetween a concavity for receiving therein a moisturizing pad. The inner and outer mask members are formed respectively with a number of breathing perforations permitting a wearer of the face mask to inhale and exhale therethrough. The moisturizing pad is retained between the outer and inner mask members at the portions having the breathing perforations and is adapted to carry a volume of water which adds moisture to air to be inhaled. The sealed bonding of the innner and outer mask members not only prevents accidental leakage of water out of the face mask, but also serves to positively hold a large volume of water for ensuring a continued moisturizing effect over a prolonged period of time.

7 Claims, 7 Drawing Sheets

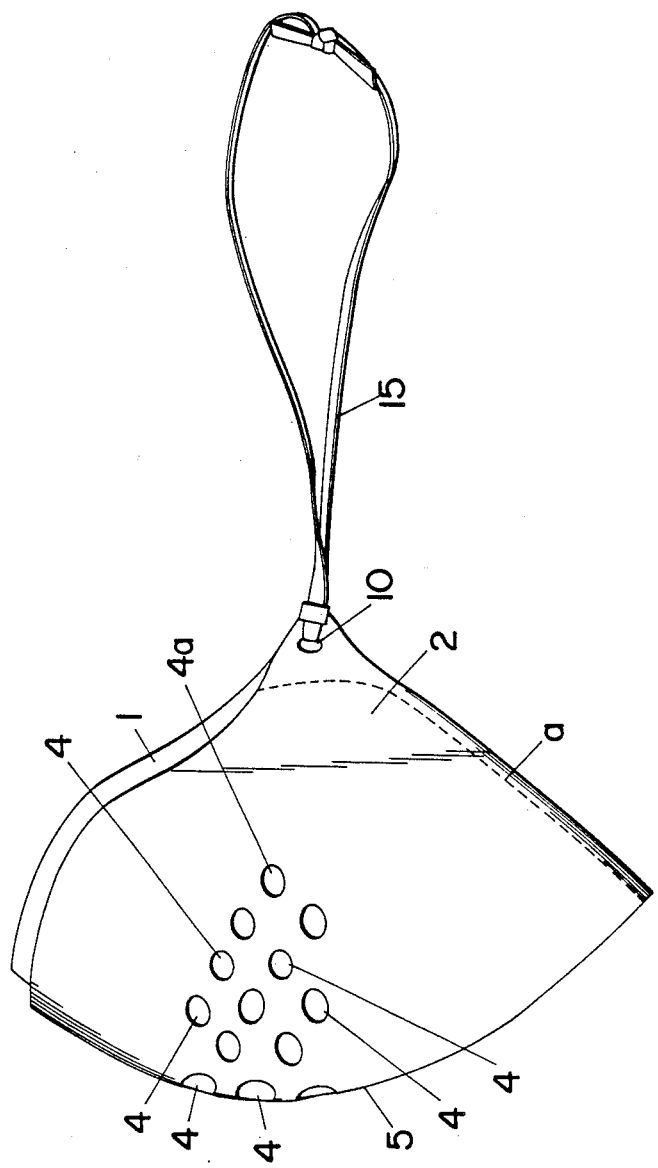

HUMIDIFICATION FACE MASK

BACKGROUND OF THE INVENTION

1. Field of the Invention

The present invention is directed to a humidification face mask for adding moisture to air inhaled through the mask.

2. Background Art

In most air conditioned environments, particularly of air liners, there is seen an excessively dried air which is very likely to afflict the humans with respiratory problems or may even afflict humans without such chronic problems by, for example, inducing inflamed throat or light pneumonia, when they are exposed to the excessively dried air condition for a longer period of time. Although there have been provided a conventional face mask with a gauze, it is contemplated simply to prevent air-laden germs from being inhaled and is not expected to protect the respiratory organs from such excessively dried air environment.

SUMMARY OF THE INVENTION

The present invention has been accomplished in view of the above problem and has a primary object to provide a humidification face mask which is capable of adding moisture to air being inhaled for protecting the respiratory organs of humans from the dried air condition.

The humidification face mask of the present invention comprises an inner mask member and an outer mask member each of which is shaped into a curved configuration for fitting over the nose and mouth of a wearer. The inner and outer mask members are provided respectively with a number of breathing perforations permitting the breathing of the wearer therethrough and are sealed together along their side and lower edges so as to leave therebetween a top opening. Inserted through the top opening and held between the inner and outer mask members is an air permeable and water absorbent moisturizing pad which carries a volume of water which moisturizes the air inhaled through the breathing perforations by the wearer. Since the inner and outer mask members are sealed along its side and lower edges, the face mask can receive a large volume of water without causing leakage of water outwardly of the mask, insuring a prolonged moisturization of the air breathed by the wearer.

In a preferred embodiment, the inner mask member is further provided on its surface facing the mouth of the wearer with a top-opened pocket for receiving therein a water absorbent recovery pad which accumulates droplets of water dripping down along the surface of the inner mask member. With this result, excess amount of moisture carried by the air which is formed as the condensation of moisture on the surface of the inner mask member adjacent the face of the wearer can be successfully recovered in the recovery pad within the pocket, preventing the dripping of such droplets on the face of the wearer and therefore insuring comfortable use of the mask over a prolonged period of time.

It is therefore another object of the present invention to provide a humidification face mask which is capable of being used over an extended period of time without causing the dripping of water on the face of the wearer.

The outer mask member is preferably formed with a plurality of tiny sharp-pointed projections which engage into the moisturizing pad for retaining the pad between the inner and outer mask members. Thus, the moisturizing pad can be firmly retained in position effective for adding moisture to the air breathed by the wearer over an extended period of time, which is therefore a further object of the present invention.

A portion of the inner mask member is bulged outwardly to define inside thereof a concavity composed of a shallow section and a deep section. The shallow section is positioned at the upper portion of the inner mask member with the breathing perforations and receives therein the moisturizing pad in open communication with the breathing perforations in the inner and outer mask members, while the deep section is positioned at the lower portion of the inner mask member having no perforations and receives therein a large volume of water preferably in the form of being carried in a bulk of water absorbent material for supplying the water to the moisturizing pad. Thus, a large volume of water can be held in the face mask to continuously moisturize the inhaled air over an extended period of time, thereby extending the effective life of the face mask, which is therefore a still further object of the present invention.

When there is a need to supply water into the mask for continued use, the water can be readily poured into the concavity by utilizing one of the breathing perforations as an inlet.

Detachable to the outer mask member is a mask cover having a number of breathing holes in open communication with the breathing perforations of the inner and outer mask members. The mask cover is secured on the outer mask member by the use of strap means for holding the face mask on the face of the wearer. The mask cover may be finished to present any desirable appearance for enhancing aesthetic appeal of the face mask, which is therefore a still further object of the present invention.

In addition to the moisturizing effect, the face mask of the present invention can be utilized to give a therapeutic effect by incorporating within the face mask a suitable medication for a respiratory disease, for example, asthma or pneumonia, to be inhaled with or without the moisturized air.

These and still other objects and advantages will become apparent from the following description of a preferred embodiment when taken in conjunction with the attached drawings.

BRIEF DESCRIPTION OF THE DRAWINGS

FIGS. 1A, 1B, and 1C are respectively a side view, a front view, and a rear view of a humidification face mask in accordance with a preferred embodiment of the present invention;

DETAILED DESCRIPTION OF THE EMBODIMENT

Figure 1B:
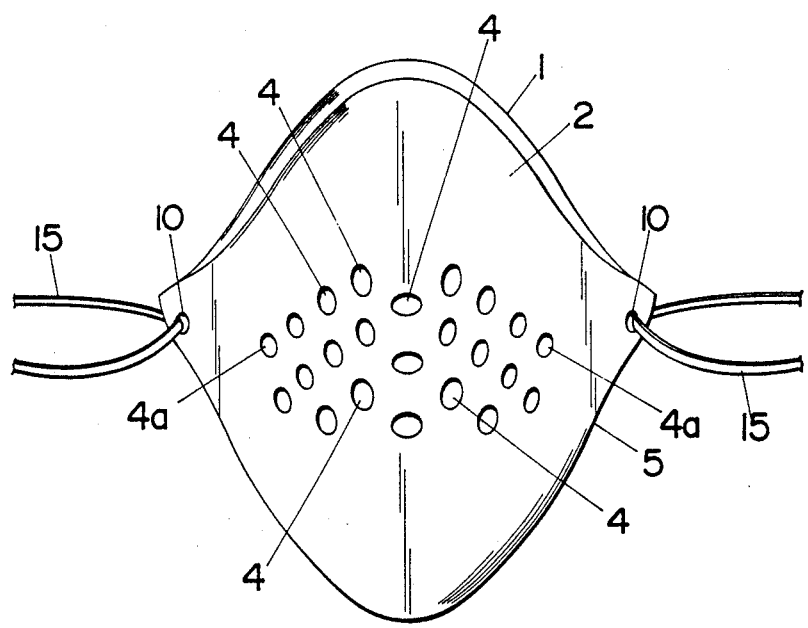
Figure 1C:
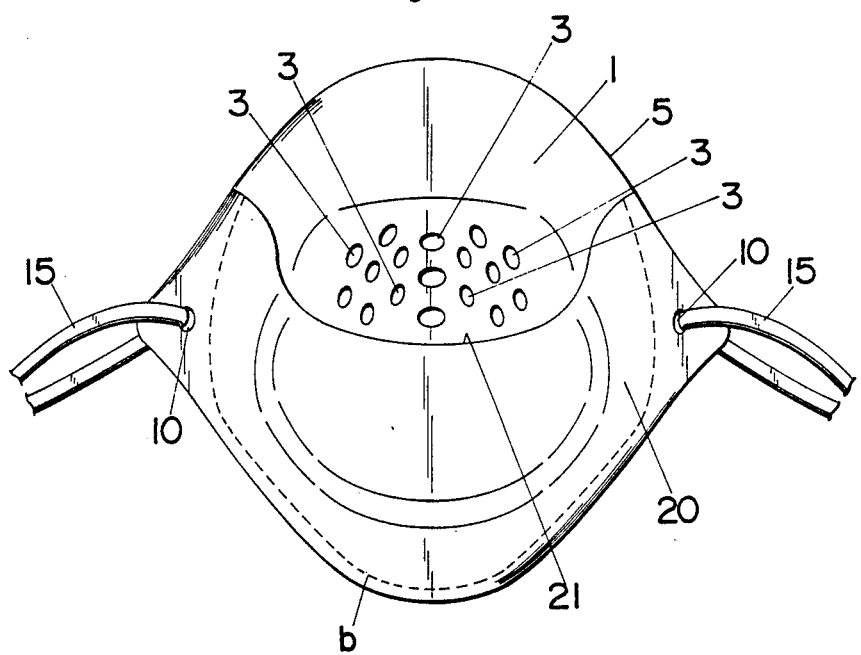
Figure 2:
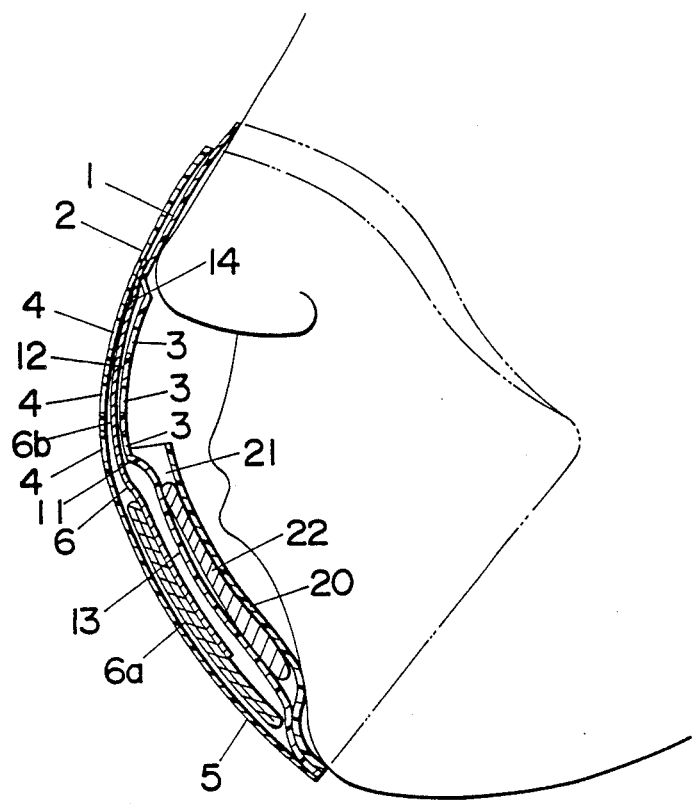
FIG. 2 is a sectional view, shown as placed on the face of a wearer, of the face mask.
Figure 3A:
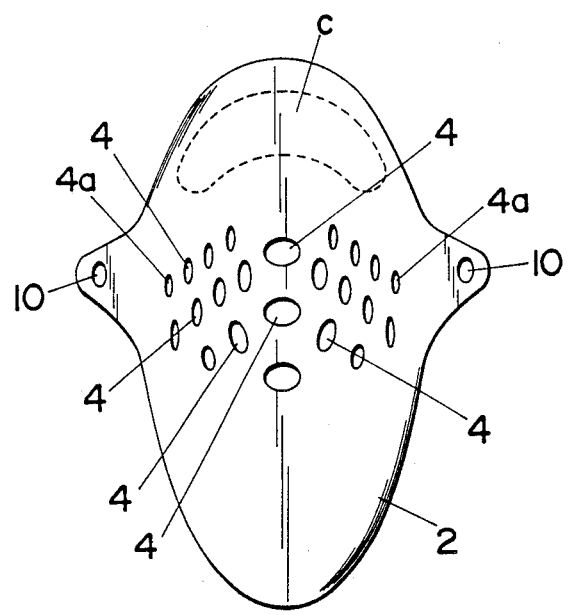
FIGS. 3A and 3B are respectively a front view and a rear view of an outer mask member of the face mask.
Figure 3B:
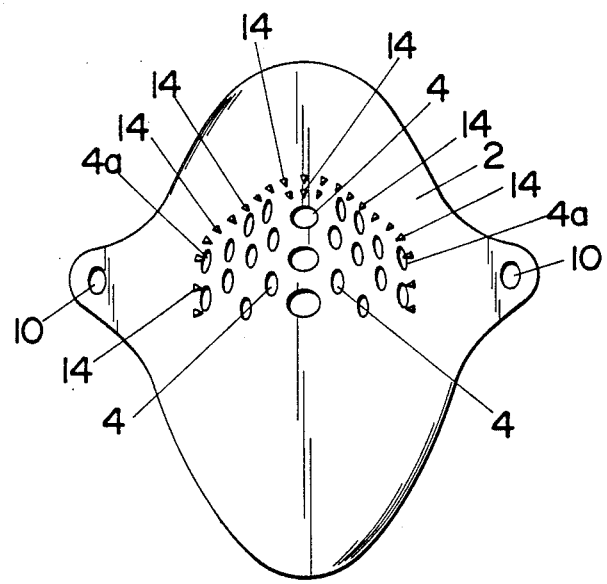
Figure 4:
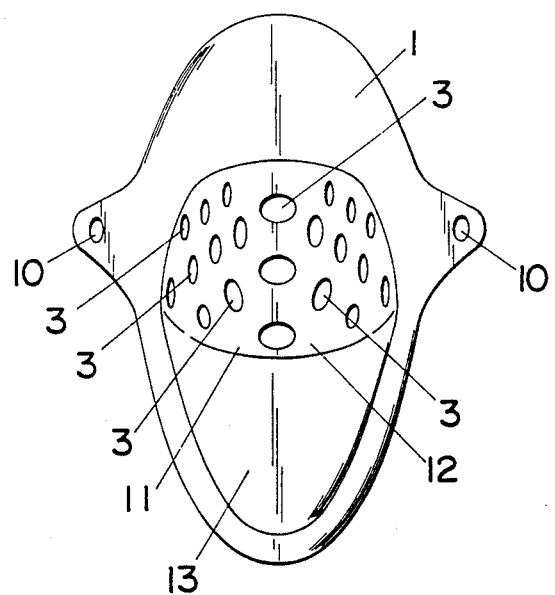
FIG. 4 is a front view of an inner mask member of the face mask.

Referring now to FIG. 1, a humidification face mask of the present invention comprises an inner mask member 1 and an outer mask member 2 both of which are made of an elastic soft or semi-hard plastic material such as polyethylene and polypropylene of water-resistant and self-shape-retaining capability. These members 1 and 2 are fabricated, for example, by the injection molding technique, into a curved configuration which conforms to a general contour of the face of a human across the nose and the mouth. As shown in FIGS. 2, 3, and 4, the inner and outer mask members 1 and 2 are respectively formed at the portion immediately below the nostrils of the wearer with a number of breathing perforations 3 and 4. These perforations 3 and 4 may be square-shaped or mesh-shaped, as well as round-shaped as illustrated in FIGS. 3 and 4. Formed at the opposite sides of each of the inner and outer mask members 1 and 2 are eyelets 10 for passing therethrough a strap 15 which places the face mask in position over the nose and mouth of the wearer. The inner mask member 1 has its major portion bulged inwardly to define inside thereof a concavity 11 which, as shown in FIGS. 2 and 4, is composed of a upper shallow section 12 and a lower deep section 13. The upper shallow section 12 is provided for retaining an air permeable and water absorbent moisturizing pad 6, while the lower deep section 13 is for holding a volume of water. Formed on the inner surface of the outer mask member 2 are a number of tiny sharp-pointed projections 14 which are disposed along the upper and side borders of the portion having the breathing perforations 4, as shown in FIG. 3B.

The inner and outer mask members 1 and 2 are placed on each other and bonded in a sealed manner along the lower and side edges (shown by a dotted line with an indication of "a" in FIG. 1A) to obtain a mask 5 of unitary construction. The inner and outer mask members 1 and 2 can be so bOnded either by heat welding or by an adhesive. Such bonding requires no particular engaging structure on the inner and outer members 1 and 2, but requires only a simple configuration to thereby facilitate the fabrication of the members 1 and 2. As shown in FIGS. 1A and 1B, the inner mask member 1 is dimensioned to have a greater height than the outer mask member 2 so that the upper edge portion of the inner mask member 1 will project slightly above that of the outer mask member 2. Also, as shown in FIG. 1C, a patch 20 of the like plastic material extends over the lower half of the inner mask member 1 and is bonded thereto in a sealed manner along its lower and side edges (shown by a dotted line with an indication of "c" in FIG. 1C) to form between the patch 20 and the outer or rear surface of the inner mask member 1 a top opened pocket 21 which is adapted to receive therein a water recovery pad 22 such as made of a gauze or the like water absorbent material. The patch 20 has a pair of eyelets 10 in registration with those of the inner and outer mask members 1 and 2 for passing therethrough the strap 15. The breathing perforations 3 of the inner mask member 1 are formed in a generally registered relationship with the breathing perforations 4 of the outer mask member 2. The outer mask member 2 is further provided with additional breathing perforations 4a, one at each side end of the upper row of the breathing perforations 4, while the inner mask member 1 has no such perforations at the portion corresponding to the additional breathing perforations 4a.

The moisturizing pad 6 is inserted into the concavity 11 through the top of the mask 5 which is opened by resiliently deforming one of the inner and outer mask members 1 and 2, and is held thereat between the inner and outer mask members 1 and 2. The moisturizing pad 6 provided is a water absorbent and air permeable material such as a cotton gauze or the like. In the illustrated embodiment, two sheets of gauze are utilized, one 6a received in the deep section 13 and the other 6b in the shallow section 12 of the concavity 11 with its lower end in touch with the gauze 6a in the deep section 13. The deep section 13 allows the gauze 6a to be received in a folded manner for supporting a large volume of water, which is continuously supplied to the gauze or moisturizing pad 6a in the shallow section 12 through the effect of capillary. Although the face mask can contain a large volume of water in the concavity 11, the water is prevented from leaking out of the mask 5 during a normal use due to the sealed bonding along the lower and side edges of the mask 5. The moisturizing pad 6b is positioned between the inner and outer mask members 1 and 2 at the respective portions having the breathing perforations 3 and 4, and is firmly held therebetween by the tiny sharp-pointed projections 14 formed on the outer mask member 2 and engaging into the moisturizing pad 6. As necessary, an additional volume of water can be supplied to the moisturizing pads 6a and 6b through one of the additional perforations 4a by the use of a suitable filler tool. In this connection, since there is no perforations formed in the inner mask member 1 at the portions corresponding to the additional perforations 4a of the outer mask member 2, the water being supplied through the perforations 4a can be prevented from splashing through the inner mask member 1.

The humidification mask thus formed is adapted in use to be held in position over the nose and mouth of the user by hooking the strap 15 around the ears, as shown in FIG. 2. With the face mask in position, air inhaled through the breathing perforations 3 and 4 by the user will also pass through the moisturizing pad 6a during which it adds moisture to the air to a suitable extent for protecting the respiratory organs from a dried air environment.

During the continued use of the mask, the moisturized air after passing through the moisturizing pad 6 is likely to cause condensation of moisture on the surface of the inner mask member 1 adjacent the face of the user and the resulting droplets of water will drip down along the surface of the inner face member 1. For preventing such droplet from sticking around the mouth and chin of the user and from giving feeling of discomfort, the recovery pad 22 serves to absorb such droplets of water leaving the user free from such discomfort caused by sticking of droplets. Each of the inner and outer mask members 1 and 2 has its upper portion bent rearwardly, in a generally L-shaped configuration as seen in horizontal section, so as to fit over the nose of the user. The bent portion (as enclosed by a dotted line with an indication of "c" in FIG. 3A) is formed to have a greater thickness than the remainder portion to improve the self-shape-retaining capability at this generally L-shaped portion, enhancing to resiliently fit this portion over the nose.

Figure 5:
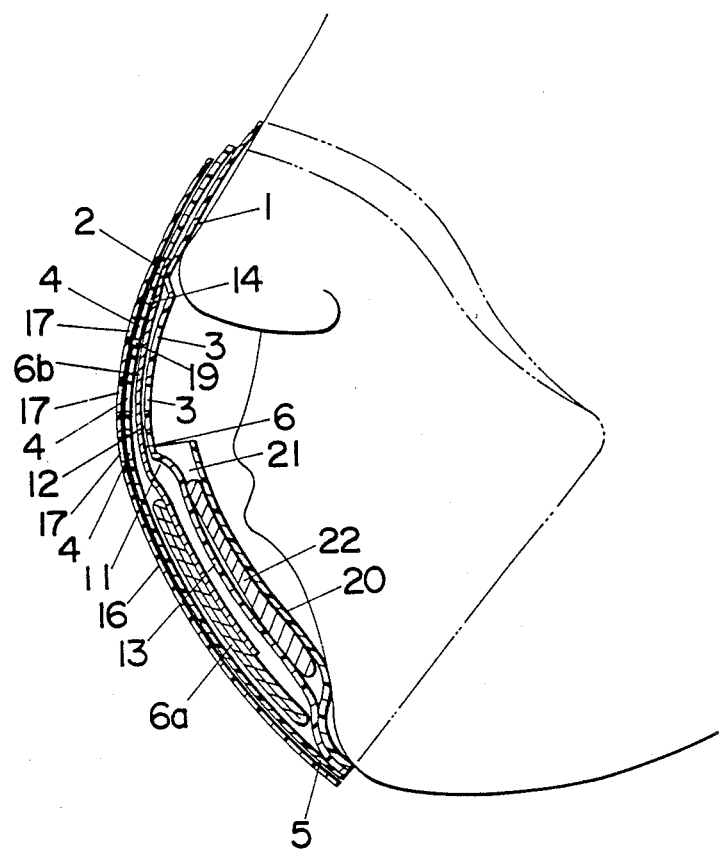
FIG. 5 is a sectional view, shown as placed on the face of a wearer, of the face mask with a mask cover attached.
Figure 6:
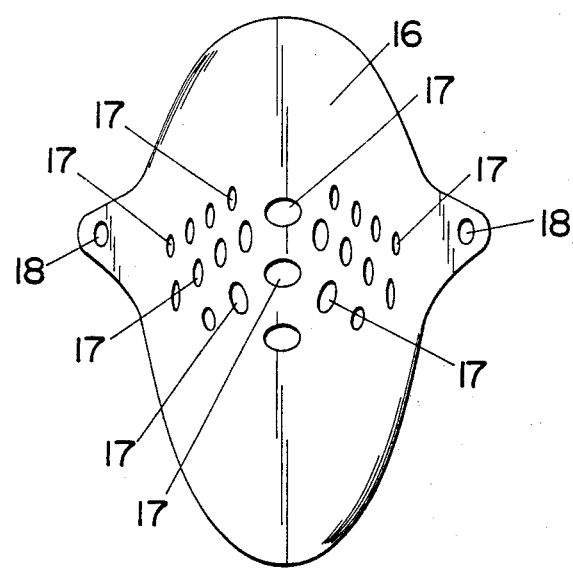
FIG. 6 is a front view of the mask cover.

Referring to FIG. 5, the face mask 5 is shown as attached with a mask cover 16. The mask cover 16 is formed to have substantially the same dimensions as the outer mask member 2 with breathing holes 17 in its center and with eyelets 18 in the opposite side ends. Since the mask cover 16 requires no substantial structural strength, it can be made thinner than the outer mask member 2. The mask cover 16 is provided to have a suitable coloring and design for adding an aesthetic appeal to the face mask 5. For example, if the face mask 5 is made in white color or transparent, the overall appearance can be suited to a desired color and/or design by the selection of the mask cover 16 among several ones of different appearances. Attachment of the mask cover 16 is effected through the operations of placing the mask cover 16 on the face mask 5, and threading the strap 15 of the face mask 5 through the eyelet 18 to secure the mask cover 16 thereat to the face mask 5. Thus, detachment of the mask cover 16 can be easily made by removing the strap 15 from the eyelet 18. The mask cover 16 is preferred to include one or more hooking elements 19 for engagement with the corresponding perforations 4 to be thereby prevented from slipping off the face mask 5.

In addition to the above moisturizing effect, the face mask of the present invention can be of course used as a conventional face mask with the moisturizing pad 6 devoid of water for preventing the entry of air-laden germs or dust.

Further, the face mask of the present invention can be utilized to give a medication effect by supporting on the moisturizing pad 6 a suitable medication for a respiratory disease, for example, asthma or pneumonia, to be inhaled with or without the moisturized air. The medication can be supported in the form of liquid, solution of solid or powder, or even volatile solid. Further, oxygen or the mixture gas thereof may be fed to the face mask 5 as a respiration aid.

What is claimed is:

1. A humidification face mask comprising: an inner mask member and an outer mask member each shaped into a curved configuration for fitting over the nose and mouth of a wearer, said inner and outer mask members provided respectively with a number of breathing perforations permitting the breathing of the wearer therethrough and being bonded together in a sealed manner along side and lower edges of said inner and outer mask members so as to leave therebetween a top opening;

an air permeable and water absorbent moisturizing pad having a first portion and a second portion inserted through said top opening and held between the inner and outer mask members, said moisturizing pad carrying a volume of water which moisturizes the air inhaled through said breathing perforations by the wearer, said inner and outer mask members forming a shallow concavity and a deep concavity therebetween, said first portion and said second portion of said moisturizing pad being accommodated within said shallow concavity and said deep concavity, respectively, and said second portion supports a large volume of water for supplying water to said first portion by capillary action; and means for supporting the face mask on the head of the wearer.

2. A humidification face mask as set forth in claim 1, wherein said inner mask member is provided on a surface facing the mouth of the wearer with a top-opened pocket for receiving therein a water absorbent recovery pad for accumulating droplets of water dripping down on said surface of the inner mask member.

3. A humidification face mask as set forth in claim 1, wherein said outer mask member is provided with a plurality of tiny sharp-pointed projections which engage into said moisturizing pad for retaining the same between the inner and outer mask members.

4. A humidification face mask as set forth in claim 1, wherein said shallow concavity and said deep concavity are formed by said inner mask member being bulged to define inside thereof said concavities for receiving said moisturizing pad between the inner and outer mask members.

5. A humidification face mask as set forth in claim 4, wherein said shallow concavity positioned at the upper portion of the inner mask member having said perforations, and said deep concavity positioned at the lower portion of said inner mask member the lower portion of said inner mask members having no perforations.

6. A humidification face mask as set forth in claim 1, further including an outer mask cover detachable to the outer mask member, said outer mask cover having a number of breathing holes in direct open communication with said perforations of the outer and inner mask members.

7. A humidification face mask as set forth in claim 1, wherein said inner and outer mask members receive therebetween a moisturizing pad having medication supported thereon for respiratory disease such as asthma or pneumonia to be inhaled with or without the moisturized air.

* * * * *